United States Patent [19]

Engelbach et al.

[11] 4,298,763
[45] Nov. 3, 1981

[54] PREPARATION OF α,β-OLEFINICALLY UNSATURATED ALDEHYDES OF 3 OR 4 CARBON ATOMS

[75] Inventors: Heinz Engelbach, Limburgerhof; Richard Krabetz, Kirchheim; Gerd Duembgen, Dannstadt-Schauernheim; Carl-Heinz Willersinn; Walter Beitelschmidt, both of Ludwigshafen, all of Fed. Rep. of Germany

[73] Assignee: BASF Aktiengesellschaft, Fed. Rep. of Germany

[21] Appl. No.: 126,896

[22] Filed: Mar. 3, 1980

[30] Foreign Application Priority Data

Mar. 12, 1979 [DE]  Fed. Rep. of Germany ....... 2909597

[51] Int. Cl.$^3$ .............................................. C07C 47/22
[52] U.S. Cl. ................................... 568/479; 568/480
[58] Field of Search ..................... 568/479, 480, 477

[56] References Cited

U.S. PATENTS DOCUMENTS

| 4,077,912 | 3/1978 | Dolhy; et al. ...................... 252/461 |
| 4,186,152 | 1/1980 | Yamamoto et al. ................ 568/454 |
| 4,195,187 | 3/1980 | Vanderspurt ....................... 568/454 |

FOREIGN PATENT DOCUMENTS

| 2135620 | 5/1976 | Fed. Rep. of Germany ...... 568/477 |
| 1529348 | 10/1978 | United Kingdom ................ 568/477 |
| 1548328 | 7/1979 | United Kingdom . |

*Primary Examiner*—Werren B. Lone
*Attorney, Agent, or Firm*—Keil & Witherspoon

[57] ABSTRACT

Acrolein and methacrolein are prepared advantageously by oxidizing propylene or isobutylene, respectively, with an oxygen-containing gas mixture under conventional conditions over a supported catalyst possessing a firmly adhering coating, from 150 to 1,500 μm thick, which contains calcined catalytic material based on molybdenum oxide and has a carrier core with a surface area of less than 15 m$^2$/g and a diameter of more than 100 μm, if a coated catalyst is used which has been prepared by applying calcined catalytic material having a particle size of from 0.1 to 300 μm, in an amount of from 1 to 40 g/min/liter of carrier and water in a weight ratio of catalytic material to water of from 1:1 to 8:1, continuously and separately from one another, each at a constant speed, at below 100° C. to vigorously agitated carrier particles which may or may not have been premoistened with water in an amount of up to 95% of the water absorbency of the particles, the prepartion of the catalyst being carried out in such a way that the water content of the coating which forms is less than the maximum degree of saturation of the catalytic material.

3 Claims, No Drawings

PREPARATION OF α,β-OLEFINICALLY UNSATURATED ALDEHYDES OF 3 OR 4 CARBON ATOMS

The present invention relates to a process for the preparation of α,β-olefinically unsaturated aldehydes of 3 or 4 carbon atoms, ie. of acrolein or methacrolein, by catalytic gas phase oxidation of the corresponding olefins, using a coated catalyst which carries a conventional catalytic material but has been prepared by an improved method.

It is known that propylene (or isobutylene) may be oxidized in the gas phase with molecular oxygen to acrolein (or methacrolein, respectively) over a catalyst which in addition to major amounts of molybdenum, iron, nickel and/or cobalt, bismuth and phosphorus may or may not contain silicon and may or may not contain small amounts of an alkali metal and/or alkaline earth metal and/or rare earth metal. Such catalysts are in general employed in multi-tube fixed bed reactors and in general in tablet form, the catalytic material in most cases being homogeneously mixed with a carrier. When the catalyst is employed in this form, problems arise, in particular at high throughput rates per unit amount of catalyst, in respect of the removal of the heat of reaction, and this in general detracts from the selectivity and the yield.

It is also known, from British Pat. No. 1,529,384 and U.S. Pat. No. 4,077,912 (Example 6) that the gas phase oxidation of propylene may be carried out with a catalyst of the above type used conjointly with a supported catalyst in which the catalytic material is applied as a coating to a carrier core. In preparing such coated catalysts, the pulverulent active material is applied to the carrier particles, for example α-Al$_2$O$_3$ balls of 0.32 cm diameter, by partially saturating the porous carrier balls with water, then coating them with the pulverulent catalytic material whilst the particles undergo a rolling motion, and then calcining the product. With such mixtures, a propylene conversion of 95 percent can be achieved in a single pass, with a high selectivity of acrolein formation, at 355° C. and a space velocity of from 1,300 to 1,700 h$^{-1}$, whilst if the catalyst in tablet form is used by itself, under corresponding conditions, a stable reaction cannot be achieved. This conventional process has the disadvantage that because of the relatively low catalytic activity of the coated catalyst prepared by the conventional process, the coated catalyst can only be employed in combination with the tablet catalyst, and at relatively low space velocities of less than 1,800 h$^{-1}$. At bath temperatures above 350° C., measures to prevent post-oxidation in the space downstream from the catalysts become less effective.

We have found that acrolein and methacrolein can be prepared particularly advantageously by oxidizing propylene and isobutylene, respectively, with an oxygen-containing gas mixture under conventional conditions over a supported catalyst possessing a firmly adhering coating, from 150 to 1,500 μm thick, which contains calcined catalytic material of the composition Mo$_{12}$Me$^1_a$Me$^2_b$Me$^3_c$Me$^4_d$Me$^5_e$O$_x$, where Me$^1$ is Bi and/or Sb, Me$^2$ is Ni, Co, Fe and/or Cu, with or without Zn and/or Mg, Me$^3$ is K, Rb, Cs and/or Tl, Me$^4$ is P and/or B, Me$^5$ is Sn, W, Nb, Ta, Cr, Pb, In and/or Na, a is from 0.1 to 13, b is from 0.5 to 15, c is from 0.01 to 4, d is from 0 to 2, e is from 0 to 3 and x is the number of oxygen atoms required to saturate the valencies of the other constituents, and a carrier core having a surface area of less than 15 m$^2$/g and a diameter of more than 100 μm, if a coated catalyst is employed which has been prepared by applying calcined catalytic material having a particle size of from 0.1 to 300 μm, in an amount of from 1 to 40 g/min/liter of carrier and water in a weight ratio of catalytic material to water of from 1:1 to 8:1, continuously and separately from one another, each at a constant speed, to vigorously agitated carrier particles which may or may not have been pre-moistened with water in an amount of up to 95% of the water absorbency of the particles, the preparation of the catalyst being carried out in such a way that the water content of the coating which forms is less than the maximum degree of saturation of the catalytic material.

In the case of the oxidation of propylene to a product consisting predominantly of acrolein, the catalytic material preferably has the composition

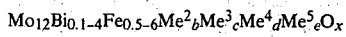

Mo$_{12}$Bi$_{0.1-4}$Fe$_{0.5-6}$Me$^2_b$Me$^3_c$Me$^4_d$Me$^5_e$O$_x$ where
Me$^2$ is nickel and/or cobalt, with or without Zn and/or magnesium,
Me$^3$ is one or more elements from the group consisting of K, Rb, Cs and/or Tl,
Me$^4$ is P,
Me$^5$ is In and/or Na and
b is from 2 to 12, preferably from 4 to 10 and, if Me$^2$ is Ni+Zn conjointly, b is from 8 to 9, whilst if Me$^2$ is Ni, b is from 5.5 to 8.5,
c is from 0.01 to 0.1, preferably from 0.03 to 0.09,
d is from 0 to 1, preferably from 0.01 to 0.2,
e is from 0 to 0.5, preferably from 0.01 to 0.2
and
x is the number of oxygen atoms required to saturate the valencies of the other constituents.

The catalytic materials which are employed for the preparation of the catalyst can be prepared in a conventional known manner by mixing aqueous solutions of preferably easily decomposable salts of the components, evaporating and/or spray-drying the mixtures, if required compressing the product, and if required calcining the product in several stages, in most cases at from 250° to 700° C., preferably in 2 stages at from 250° to 400° C. and from 480° to 660° C. respectively, and milling the product to a particle size which is in general from 0.1 to 300, preferably from 0.2 to 150, especially from 0.5 to 50, μm.

The pulverulent calcined catalytic material is then applied as a coating to the vigorously agitated carrier particles which have been pre-moistened with water, and at the same time water is applied, generally sprayed, onto the carrier particles, the rate of application of the catalyst powder and of the water each being constant. The amount of calcined catalytic material applied per minute per liter of carrier is from 1 to 40, preferably from 2 to 25, g. The material can for example be applied onto the carrier particles, which are being vigorously agitated in a rotating dish or a coating drum, by means of a metering belt weigher and/or metering screw with vibratory chute and distributing device, the water being sprayed onto the carrier particles simultaneously, but spatially separate from the catalytic material. The pulverulent catalytic material should impinge on the rolling carrier particles outside the spray cone of the water, and the weight ratio of catalyst powder to water should preferably be from 2:1 to 5:1. The porous carrier particles should be premoistened with at least 0.1%, of their weight, of water, but in general the pre-moistening should not exceed 95% of the water absorbency of the particles. The water absorbency is the maximum amount of water in g which 100 g of the carrier particles, in the form in which they are employed for the preparation of the catalyst, can absorb. The degree of pre-moistening depends on the porosity of the carrier particles and should, for the preferred porosities of less than 5%, only be from about 0.1 to 2 percent by weight, based on the carrier particles, and should not exceed 95% of the water absorbency. With porosities greater than 5%, pre-moistening with from 5 to 30, preferably from 10 to 25, % of the water absorbency of the carrier is advantageous. Nonporous carrier particles do not have to be pre-moistened. The carrier particles, which can consist of the conventional materials, for example of α-aluminum oxide, silicon dioxide, silicates, eg. magnesium silicate and magnesium aluminum silicate, and silicon carbide, should preferably have a surface area of less than 15 m$^2$/g, especially less than 5 m$^2$/g. The carrier materials may or may not be molded; the use of balls of diameter from 0.5 to 6 mm, preferably from 1 to 5 mm, is preferred. It is advantageous if the carrier particles have a porosity of less than 5% and possess a natural or artificial surface roughness. The amount of catalytic material in the coated catalyst employed for the novel process is from 50 to 250% by weight, preferably from 55 to 200% by weight, especially—in the case of catalysts for isobutene oxidation—from 100 to 180% by weight, based on the weight of carrier, and the thickness of coating should in general be from 150 to 1,500 μm, preferably from 300 to 1,200 μm. In the coating method according to the invention, the degree of moistening of the coating which forms on the carrier particles should, during the coating process, in general be from 40 to 95%, preferably from 50 to 90%, of the maximum degree of saturation. The maximum degree of saturation of the coating corresponds to a moisture content at which the partially coated carrier particles start to agglomerate, ie. no longer roll as isolated particles in the coating apparatus. As an approximation, the maximum degree of saturation of the coating is the amount of water in g which is taken up by 100 g of the stirred catalyst powder before the agglomerates, formed on dropwise addition of water, become superficially moist and tacky. Before use for the oxidation of olefins, the coated catalyst is dried to a water content of from 0.1 to 2% of its weight, in general at below 150° C. Whilst calcining the catalyst at a higher temperature, for example at from 400° to 700° C., is possible, it is generally not necessary.

The novel oxidation process can be carried out in the conventional tubular reactors in which the reaction tubes in general have a diameter of from 15 to 25 mm and are surrounded by a flowing molten salt mixture as the heat transfer medium. The novel process is in general operated in the conventional pressure range of from 1.2 to 3 bar. In the case of the oxidation of propylene, for example, the gas entering the reactor in general has the conventional composition of from 3 to 8 percent by volume of propylene and from 6 to 12 percent by volume of oxygen, with from 80 to 91 percent by volume of inert gases, for example water vapor, nitrogen, carbon monoxide or carbon dioxide.

For the oxidation of propylene, the salt bath temperatures are in most cases from 300° to 350° C., preferably from 310° to 340° C., whilst for the oxidation of isobu-tene they are from 350° to 450° C. When using the coated catalysts prepared according to the invention, the conjoint use of conventional non-coated supported catalysts, such as is disclosed in German Laid-Open Application DOS No. 2,611,249, is feasible, but not necessary. However, it is advantageous to arrange coated catalysts having different contents of active material and hence different activities in a reaction tube in such a way that the activity increases continuously or stepwise in the direction of flow. The novel process permits the use of particularly high throughputs per unit amount of catalyst and hence achieves high space-time yields; at the same time, surprisingly, the formation of undesired by-products is in some cases less than in the conventional processes. In the novel process, the reaction mixture can be directly oxidized further in a conventional manner, with or without addition of more oxygen and/or diluents, in an additional reactor which contains a specific catalyst, (which may or may not be of a conventional type), for the purpose, substantially giving acrylic acid (or methacrylic acid); the residual gas obtained can, after removal of the reaction products and by-products and, where appropriate, after removal of water, be recycled to the inlet of the propylene (or isobutene) oxidation reactor, and be mixed, at that point, with fresh gas.

The *maximum degrees of saturation*, referred to in the Examples which follow, of the pulverulent calcined catalytic material are determined as follows:

Water is added, in the course of from 5 to 10 minutes, to 100 g of the catalyst powder, stirred in a porcelain dish, until the agglomerates which form have completely taken up the pulverulent constitutents, and become superficially moist and tacky. The water consumption, based on weight of dry powder, determined by re-weighing represents the maximum degree saturation.

The *water absorbency of the carrier*, referred to in the Examples which follow, is determined as follows:

100 g of the carrier, in the form present during preparation of the catalyst, are saturated under water and filled into a slightly moistened paper filter, and the excess water is allowed to drain off for 15 minutes. The weight increase of the carrier, based on the dry weight of carrier, represents the water absorbency of the carrier.

In the Examples which follow, percentages are by weight.

EXAMPLE 1

(a) Preparation of the catalyst

A catalytic material having the composition

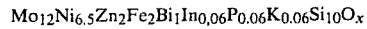

$Mo_{12}Ni_{6.5}Zn_2Fe_2Bi_1In_{0.06}P_{0.06}K_{0.06}Si_{10}O_x$ is prepared as follows:

561 g of bismuth nitrate solution (11% of Bi, 5% of free nitric acid), 854 g of nickel nitrate solution (13.2% of nickel), 239 g of iron nitrate, 176 g of zinc nitrate and 18.4 g of indium nitrate (11% indium) are mixed, in the stated sequence, into 1,240 g of water. A solution of 625 g of ammonium heptamolybdate and 2.3 g of 75% strength phosphoric acid as well as 544 g of 25% strength ammonia solution and potassium hydroxide in an amount corresponding to 80 ppm of potassium based on this molybdate solution in 3,320 g of water is added to the above nitrate solution. 354 g of 50% strength aqueous silica sol are then added and the resulting suspension is spray-dried.

500 g of the spray-dried material are kneaded with 62 g of water and 0.34 g of 48% strength potassium hydroxide solution for 1½ hours and then molded to give extrudates of 4.5 mm diameter. The extrudates are dried for 24 hours at 120° C., then calcined for 2 hours at 360° C. in the presence of air and subsequently milled to a particle size of less than 300 μm. The maximum degree of saturation of the calcined catalytic powder is 48%. This powder is mixed with 6% by weight of Pharmacoat.

2,600 g of the powder are charged at the rate of 17.4 g/liter of carrier/minute onto 2,500 g (1.78 liters) of carrier particles which have been pre-moistened with 32 g of water, and at the same time 850 g of water are sprayed in continuously, but spatially separate from the powder, through a nozzle at a speed of 5.9 g per liter of carrier per minute. The carrier used consists of commercial magnesium silicate balls of diameter from 1.5 to 2.5 mm, having a porosity of about 1%. The coating is carried out on a rotating dish of 50 cm diameter, running at 14 rpm. The mean degree of moistening of the coating which forms is 71% of the maximum degree of saturation. After completion of coating, the coated catalyst obtained is dried for 16 hours at 80° C. and then calcined in a stream of air at 600° C. for 1½ hours.

(b) Oxidation of propylene to acrolein 800 cm³ of the coated catalyst obtained as described in (a) are heated at 342°–343° C. in a steel tube of 3.6 m length and 21 mm internal diameter. Per hour, a mixture of 80 liters (S.T.P.) of propylene, 800 liters (S.T.P.) of air and 800 liters (S.T.P.) of nitrogen is passed over the heated catalyst. A propylene conversion of 95.3 mole percent, an acrolein yield of 83.5 mole percent and an acrylic acid yield of 6 mole percent is obtained. The selectivity in respect of acrolein and acrylic acid is thus 3.9%.

At a reaction temperature of 332° C., under otherwise identical conditions, a propylene conversion of 87.8 mole percent, a combined yield of acrolein and acrylic acid of 83.7 mole percent and a combined selectivity of 95.3 mole percent are achieved.

In a further experiment, in which the throughput is increased to 96 liters (S.T.P.) of propylene, 960 liters (S.T.P.) of air and 960 liters (S.T.P.) of nitrogen, at a bath temperature of 340° C. but under otherwise identical conditions, a conversion of 95 mole %, a combined yield of acrolein and acrylic acid of 88.7 mole % and a combined selectivity of 93.4 mole % are achieved.

(c) Other coated catalysts, and their use for the oxidation of propylene.

Catalytic materials having the following composition
$Mo_{12}Ni_{8.5}Fe_2Bi_1P_{0.06}K_{0.06}Si_{10}O_x$,
$Mo_{12}Ni_{5.5}Zn_2Fe_2Bi_1P_{0.05}Rb_{0.06}Si_{10}O_x$ and
$Mo_{12}Ni_{6.5}Zn_2Fe_2Bi_1P_{0.06}In_{0.065}K_{0.06}Na_{0.2}Si_{10}O_x$
are prepared as described under (a) and applied, in amounts of 140 g per 100 g of carrier, to the magnesium silicate balls. The catalysts obtained are very abrasion-resistant and are, for example, very suitable for the oxidation of propylene to acrolein under the conditions described in (b).

EXAMPLE 2

(a) Preparation of the catalyst

A catalytic material having the composition $Mo_{12}Bi_1Fe_3Ni_1Co_7B_2Sb_{0.1}K_{0.14}O_{56.7}$ is prepared as described in Example 1 of British Pat. No. 1,491,750. The resulting catalytic material is milled to a particle size of less than 30 μm. The maximum degree of saturation of the catalyst powder is 33.4%.

156 g of the catalytic powder are applied continuously, at a constant speed of 17.3 g per liter of carrier per minute, to 100 g (corresponding to 76 cm³) of nonporous steatite balls of 3 mm diameter which are pre-moistened with 1 g of water, on a rotating dish of 30 cm diameter, and simultaneously but separately therefrom 6.9 g of water per liter of carrier per minute are sprayed continuously, at a constant speed, onto the balls at 20°–25° C. 12.5 liters (S.T.P.) of air per minute are employed for spraying the water. The dish rotates at 35 rpm. Under the stated conditions, the water content of the coating which forms is 67% of the maximum degree of saturation of the catalytic powder. The coated catalyst obtained has a mean particle diameter of 4.7 mm, corresponding to a mean coating thickness of 0.85 mm. The abrasion resistance of the catalyst is very good.

(b) Oxidation of isobutene to methacrolein 43 cm³ of the coated catalyst are heated at 376° C. in a steel tube of 15 mm internal diameter and per hour a mixture of 3 liters (S.T.P.) of isobutylene, 37.2 liters (S.T.P.) of air and 24 liters (S.T.P.) of steam is passed over the catalyst. This gives a conversion of isobutene of 94 mole percent, a methacrolein yield of 80 mole percent and a methacrylic acid yield of 1 mole percent, corresponding to a total selectivity of 87 mole percent.

(c) Other coated catalysts and their use for the oxidation of isobutylene

Catalytic materials are prepared as described in Examples 2, 6, 9 and 18 of British Pat. No. 1,490,683 and applied, as described under (a), to the magnesium silicate balls in amounts of 150 g of catalytic material per 100 g of carrier. The coated catalysts are very suitable for the oxidation of isobutene to methacrolein.

We claim:
1. In a process for the preparation of acrolein or methacrolein by oxidation of propylene or isobutylene with an oxygen-containing gas mixture under conventional conditions over a supported catalyst possessing a firmly adhering coating, from 150 to 1,500 μm thick, which contains calcined catalytic material of the composition

$$Mo_{12}Bi_{0.1-4}Fe_{0.5-6}P_{0-1}Me_b^2Me_c^3Me_e^5O_x$$

where $Me^2$ is Ni and Zn, $Me^3$ is K, Rb and/or Cs, $Me^5$ is In and/or Na, b is 8 to 9, b for Ni being 5.5 to 8.5, c is from 0.01 to 0.1, e is from 0.01 to 0.2, and x is the number of oxygen atoms required to saturate the valencies of the other constituents, and a carrier core having a surface area of less than 15 m²/g and a diameter of more than 100 μm, the improvement that the coated catalyst employed has been prepared by applying calcined catalytic material having a particle size of from 0.1 to 300 μm, in an amount of from 1 to 40 g/min/liter of carrier and water in a weight ratio of catalytic material to water of from 1:1 to 8:1, continuously and separately from one another, each at a constant speed, to vigorously agitated carrier particles which may or may not have been pre-moistened with water in an amount of up to 95% of the water absorbency of the particles, the preparation of the catalyst being carrier out in such a way that the water content of the coating which forms is less than the maximum degree of saturation of the catalytic material.

2. The process of claim 1, wherein the carrier of the coated catalyst has a porosity of less than 5% and has been moistened with from 0.1 to 2%, of its weight, of water before being charged with the catalytic material.

3. The process of claim 1, wherein the carrier of the coated catalyst has a porosity of more than 5% and has been moistened with from 10 to 30%, of its water absorbency, of water before being charged with the catalytic material.

* * * * *

UNITED STATES PATENT AND TRADEMARK OFFICE
CERTIFICATE OF CORRECTION

PATENT NO. : 4,298,763
DATED : November 3, 1981
INVENTOR(S) : H. Engelbach, R. Krabetz, G. Duembgen, C.H. Willersinn and W. Beitelschmidt It is certified that error appears in the above—identified patent and that said Letters Patent is hereby corrected as shown below:

IN THE CLAIMS

Claim 1, line 67 of column 6, "carrier" should read --carried--.

Signed and Sealed this

Thirtieth Day of March 1982

[SEAL]

Attest:

Attesting Officer

GERALD J. MOSSINGHOFF

Commissioner of Patents and Trademarks